(12) United States Patent
Walton et al.

(10) Patent No.: US 10,130,739 B2
(45) Date of Patent: Nov. 20, 2018

(54) FLEXIBLE, ULTRASOUND-COUPLED DEVICES AND METHODS FOR ASPIRATING BIOLOGICAL TISSUE

(71) Applicants: Chad Walton, Honolulu, HI (US); Rich Allsop, Kapolei, HI (US); Mark T Khemmani, Honolulu, HI (US)

(72) Inventors: Chad Walton, Honolulu, HI (US); Rich Allsop, Kapolei, HI (US); Mark T Khemmani, Honolulu, HI (US)

( * ) Notice: Subject to any disclaimer, the term of this patent is extended or adjusted under 35 U.S.C. 154(b) by 0 days.

(21) Appl. No.: 14/093,185

(22) Filed: Nov. 29, 2013

(65) Prior Publication Data

US 2014/0148832 A1    May 29, 2014

Related U.S. Application Data

(60) Provisional application No. 61/731,228, filed on Nov. 29, 2012.

(51) Int. Cl.
*A61M 1/00* (2006.01)
*A61B 10/02* (2006.01)
(Continued)

(52) U.S. Cl.
CPC ........... *A61M 1/008* (2013.01); *A61B 10/025* (2013.01); *A61B 17/2202* (2013.01); *A61N 7/02* (2013.01);
(Continued)

(58) Field of Classification Search
CPC . A61B 17/22012; A61B 18/245; A61B 19/54; A61B 17/22; A61B 2218/001; A61B 2218/007; A61B 2017/00292; A61B 2017/22015; A61B 2017/22065; A61B 2017/320076; A61B 17/320068; A61B 2017/32008; A61B 2017/320084; A61B 2017/320088; A61B 17/320096; A61B 2017/320072; A61B 10/025;
(Continued)

(56) References Cited

U.S. PATENT DOCUMENTS 4,526,571 A * 7/1985 Wuchinich ...................... 604/22
5,318,014 A * 6/1994 Carter ................. A61B 17/2202
604/22
(Continued)

*Primary Examiner* — Eric Rosen
*Assistant Examiner* — Mikail Mannan
(74) *Attorney, Agent, or Firm* — Tarolli, Sundheim, Covell & Tummino LLP

(57) ABSTRACT

One aspect of the present disclosure relates to a device for aspirating a biological tissue from a subject. The device can comprise a flexible, hollow shaft and an ultrasound assembly. The shaft can have a central portion that extends between a proximal end and a distal end thereof. The shaft can include a first lumen that extends between the proximal and distal ends. The ultrasound assembly can be connected to the distal end of the shaft. The ultrasound assembly can include a casing, at least one ultrasound transducer disposed within the casing, and a second lumen that extends through the ultrasound assembly and is in fluid communication with the first lumen. The at least one ultrasound transducer can be configured to generate acoustical waves having an intensity and frequency sufficient to disrupt, but not substantially damage, the biological tissue so that the biological tissue can be aspirated through the device.

9 Claims, 14 Drawing Sheets

(51) Int. Cl.
*A61B 17/22* (2006.01)
*A61N 7/02* (2006.01)

(52) U.S. Cl.
CPC ............... *A61B 2010/0258* (2013.01); *A61B 2017/22024* (2013.01); *A61B 2217/005* (2013.01)

(58) Field of Classification Search
CPC ........ A61B 17/2202; A61B 2010/0258; A61B 2017/22024; A61B 2217/005; A61M 1/008; A61M 1/0086; A61M 1/0088; A61M 1/009; A61M 1/0092; A61N 7/02; A61F 9/00745; A61F 9/00754
USPC ......... 606/169–172; 600/466, 469, 571, 573, 600/578, 562–568; 604/22, 19, 35, 118, 604/131, 317, 33, 187, 93.01–99.03, 523, 604/540–543, 119; 601/2; 433/119; 128/916
See application file for complete search history.

(56) References Cited

U.S. PATENT DOCUMENTS

| | | | |
|---|---|---|---|
| 5,474,530 A * | 12/1995 | Passafaro et al. | 604/22 |
| 5,651,366 A * | 7/1997 | Liang et al. | 600/439 |
| 5,957,882 A * | 9/1999 | Nita et al. | 604/22 |
| 6,024,718 A | 2/2000 | Chen et al. | |
| 6,361,531 B1* | 3/2002 | Hissong | 606/27 |
| 6,419,659 B1* | 7/2002 | Phelps et al. | 604/164.01 |
| 6,433,464 B2* | 8/2002 | Jones | 310/328 |
| 6,514,249 B1* | 2/2003 | Maguire et al. | 606/41 |
| 6,607,502 B1* | 8/2003 | Maguire et al. | 604/22 |
| 6,685,657 B2* | 2/2004 | Jones | A61B 17/22012 601/2 |
| 7,387,612 B2* | 6/2008 | Pal | A61B 17/16 601/2 |
| 2003/0225364 A1* | 12/2003 | Kraft | A61B 10/025 604/35 |
| 2007/0025919 A1* | 2/2007 | Deem | A61K 38/164 424/45 |
| 2007/0249942 A1* | 10/2007 | Salehi | A61F 9/00745 600/471 |
| 2007/0276352 A1* | 11/2007 | Crocker et al. | 604/500 |
| 2009/0131827 A1* | 5/2009 | Crocker et al. | 600/571 |
| 2009/0306549 A1* | 12/2009 | MacAdam et al. | 601/2 |
| 2012/0078164 A1 | 3/2012 | Mulvihill et al. | |
| 2013/0253387 A1* | 9/2013 | Bonutti | A61H 23/0245 601/46 |

* cited by examiner

FLEXIBLE, ULTRASOUND-COUPLED DEVICES AND METHODS FOR ASPIRATING BIOLOGICAL TISSUE

RELATED APPLICATION

This application claims the benefit of U.S. Provisional Patent Application Ser. No. 61/731,228, filed Nov. 29, 2012, the entirety of which is hereby incorporated by reference for all purposes.

TECHNICAL FIELD

The present disclosure relates generally to devices and methods for removing biological tissue and, more particularly, to devices and methods for aspirating biological tissue utilizing acoustical waves during a surgical procedure.

BACKGROUND

Bone marrow is a tissue which resembles blood and is found in the center of flat-type bones. Several types of stem cells, including all hematopoietic stem cells, reside in bone marrow. Stem cells are precursors to functional, mature cells, such as red and white blood cells and platelets. Stem cells, in particular, are important because they are responsible for sustaining and replenishing all mature cells in a specific type of organ throughout life. There are certain blood-related disorders (both cancerous and non-cancerous) where a bone marrow transplant is needed. These diseases cause the body's stem cells to not produce the right amount of blood cells or cause them to be defective. Such diseases include leukemia, lymphoma, and other cancers. Non-cancerous diseases like sickle cell anemia and thalassemia also require bone marrow transplants.

The extraction of bone marrow for long-term storage in deep freeze banks is becoming more and more common. These stored reserves may be used at times of serious injury to replenish one's own blood, for example. The traditional way of harvesting bone marrow is done by using a needle that requires several incisions into the tissue and bore sites through the iliac crest bone (i.e., pelvic bone). Approximately 500-1200 ml of bone marrow needs to be harvested. On average, this means about 5-6 holes are bore into the bone during each harvest, drawing out 100-200 ml of bone marrow from each site. Each site is limited to this amount of bone marrow as a result of the syringe used for such procedures, which, due to its size, creates only a small amount of negative pressure. Additionally, the needles used only permit bone marrow aspiration in the immediate vicinity of the needle tip. Consequently, such drawbacks increase the cost, amount of patient trauma, and degree procedural complexity associated with conventional methods for harvesting bone marrow.

SUMMARY

The present disclosure relates generally to devices and methods for removing biological tissue and, more particularly, to devices and methods for aspirating biological tissue utilizing acoustical waves during a surgical procedure.

One aspect of the present disclosure relates to a device for aspirating a biological tissue from a subject. The device can comprise a flexible, hollow shaft and an ultrasound assembly. The shaft can have a central portion that extends between a proximal end and a distal end thereof. The shaft can include a first lumen that extends between the proximal end and the distal end. The ultrasound assembly can be connected to the distal end of the shaft. The ultrasound assembly can include a casing, at least one ultrasound transducer disposed within the casing, and a second lumen that extends through the ultrasound assembly and is in fluid communication with the first lumen. The at least one ultrasound transducer can be configured to generate acoustical waves having an intensity and frequency sufficient to disrupt, but not substantially damage, the biological tissue so that the biological tissue can be aspirated through the device.

Another aspect of the present disclosure relates to a device for aspirating a biological tissue from a subject. The device can comprise a flexible, hollow shaft and a plurality of axially aligned ultrasound transducer assemblies. The shaft can have a central body portion that extends between a proximal end portion and a distal end portion thereof. The shaft can include a first lumen extending between the proximal and distal end portions. The plurality of ultrasound transducer assemblies can be disposed within the distal end portion of the shaft. Each of the ultrasound assemblies can include a casing and at least one ultrasound transducer disposed within the casing. The plurality of ultrasound assemblies can define a second lumen that is in fluid communication with the first lumen. Each of the ultrasound transducers can be configured to generate acoustical waves having an intensity and frequency sufficient to disrupt, but not substantially damage, the biological tissue so that the biological tissue can be aspirated through the device.

Another aspect of the present disclosure relates to a method for aspirating a biological tissue from a subject. One step of the method can comprise providing a device that includes a flexible, hollow shaft and an ultrasound assembly connected to a distal end of the shaft. The ultrasound assembly can include at least one ultrasound transducer disposed in a casing. Next, the ultrasound assembly can be placed into contact with the biological tissue. A series of acoustical waves, generated by the at least one ultrasound transducer, can then be applied to the biological tissue. The generated acoustical waves can have a frequency and intensity sufficient to disrupt, but not substantially damage, the biological tissue. Disrupted biological tissue can be aspirated through the device.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1A:
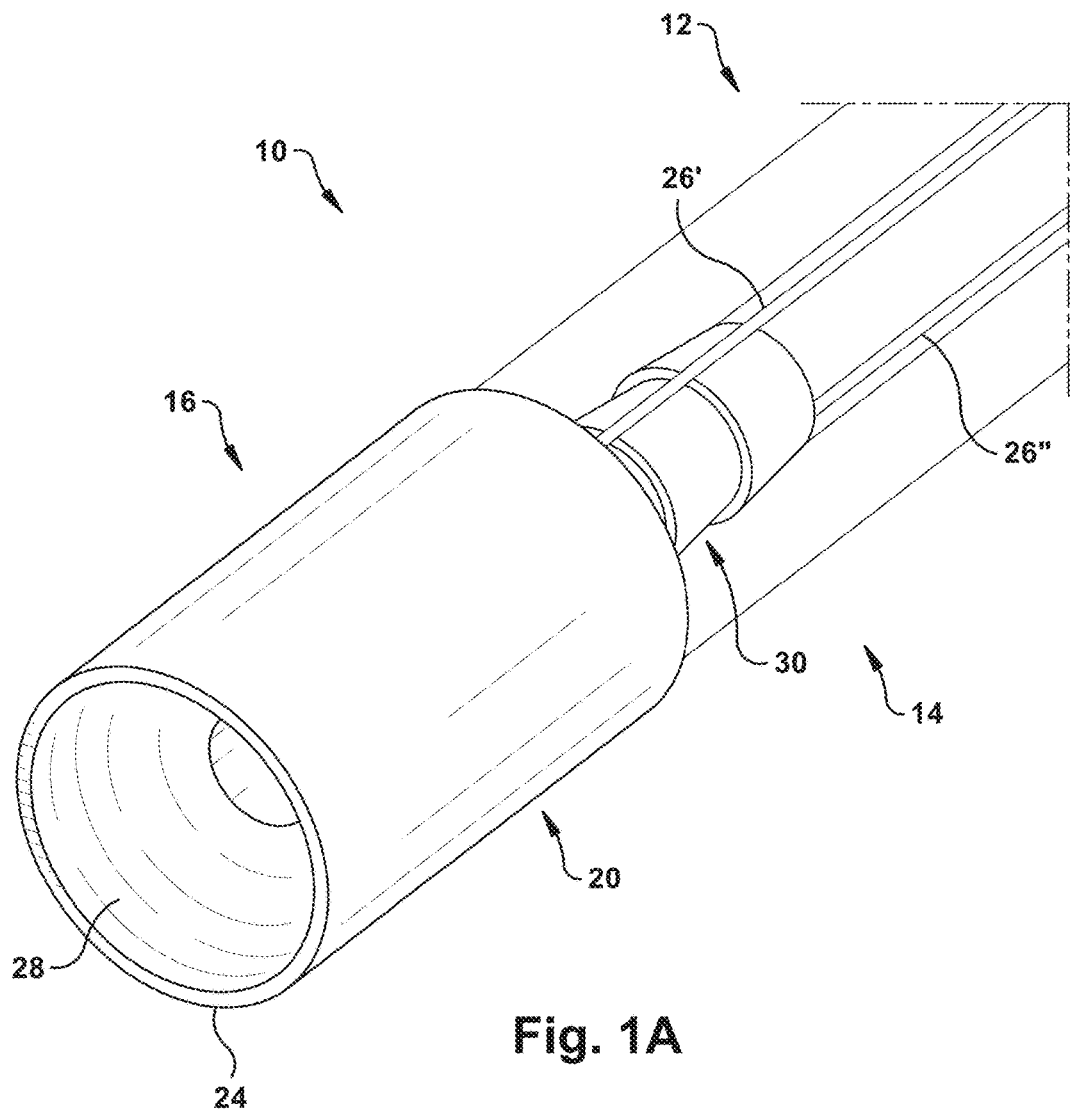
FIGS. 1A-B are perspective views showing assembled (FIG. 1A) and exploded (FIG. 1B) configurations of a device for aspirating a biological tissue from a subject constructed in accordance with one aspect of the present disclosure.

Unless defined otherwise, all technical and scientific terms used herein have the same meaning as is commonly understood by one of skill in the art to which the present disclosure pertains.

In the context of the present disclosure, the term "subject" can refer to any warm or cold-blooded organism including, but not limited to, human beings, pigs, rats, mice, dogs, goats, sheep, horses, monkeys, apes, rabbits, cattle, birds, marine mammals, fish, reptiles, amphibians, etc.

When an element or structure is referred to herein as being "on," "engaged to," "connected to," "attached to", or "coupled to" another element or structure, it may be directly on, engaged, connected or coupled to the other element or structure, or intervening elements or structures may be present. In contrast, when an element is referred to as being "directly on," "directly engaged to," "directly connected to," or "directly coupled to" another element or structure, there may be no intervening elements or structures present. Other words used to describe the relationship between elements should be interpreted in a like fashion (e.g., "between" versus "directly between," "adjacent" versus "directly adjacent," etc.).

As used herein, the term "ultrasound transducer" can refer to any device, component, structure, or material that is capable of projecting ultrasound energy. Typically, an ultrasound transducer is an electrical device that includes a piezoelectric element, such as a thin crystal, that converts electrical signals into acoustical waves. However, examples of alternative types of ultrasound transducers that can be used in practice of the present disclosure can include magnetostrictive or electrostrictive devices and non-linear laser effects that produce an acoustico-optical effect. One or more such ultrasound transducers can be used simultaneously to accomplish the goals of the present disclosure.

As used herein, the term "hard tissue" can refer to hard biological materials from living organisms. Non-limiting examples can include bone, cartilage, teeth, nails, hair, etc.

As used herein, the term "soft tissue" can refer to soft biological materials from living organisms. Non-limiting examples can include bone marrow, hepatic tissue, pancreatic tissue, brain tissue, renal tissue, pulmonary tissue, testicular tissue, ovarian tissue, dermal tissue, lymphatic tissue, splenic tissue, adipose tissue (e.g., fat cells), tumor tissue (e.g., cancer cells), and stem and/or progenitor cells from any soft tissue.

As used herein, the terms "disrupt" or "disruption" with regard to the effect of acoustical waves on a biological tissue can refer to dissociation or separation of a cell or cells comprising the biological tissue from other cells and/or hard or soft tissue structures associated with the cell(s) such that one or more of the cells can be readily removed (e.g., aspirated) according to the present disclosure.

As used herein, the terms "substantially damage" or "substantially damaged" when used with regard to a disrupted biological tissue can mean that a certain number, ratio (e.g., viable to dead cells), or percentage of cells comprising the disrupted biological tissue are viable (e.g., capable of division, differentiation, adhesion, factor secretion, etc.). Assays for evaluating cell viability are known in the art and can include, for example, Trypan Blue staining. In some instances, the percentage of viable cells present in a disrupted biological tissue can be about 100%, about 95%, about 90%, about 85%, about 80%, about 75%, about 70%, or less.

As used herein, the terms "impedance-matched material" or "impedance-matched materials" can refer to any one or combination of materials used to coax or transmit energy (e.g., ultrasonic energy or acoustical waves) between two different materials having two different respective impedances so that the energy is transferred across the border between the materials and not reflected or absorbed. Sound travels through materials under the influence of sound pressure. Because molecules or atoms of a solid are bound elastically to one another, the excess pressure results in a wave propagating through the solid. The acoustic impedance (Z) of a material is defined as the product of its density (p) and acoustic velocity (V), which can be expressed as $Z=pV$. Acoustic impedance is important in the determination of acoustic transmission and reflection at the boundary of two materials having different acoustic impedances, which can find application in the design of ultrasonic transducers and assessing absorption of sound in a medium. As noted above, acoustic impedance of the two media are very different most sound energy will be reflected (or absorbed), rather than transferred across the border (see, e.g., Education Resource Center, 2001-2012, The Collaboration for NDT Education, Iowa State University, www.ndt-ed.org.).

Overview

Figure 1B:
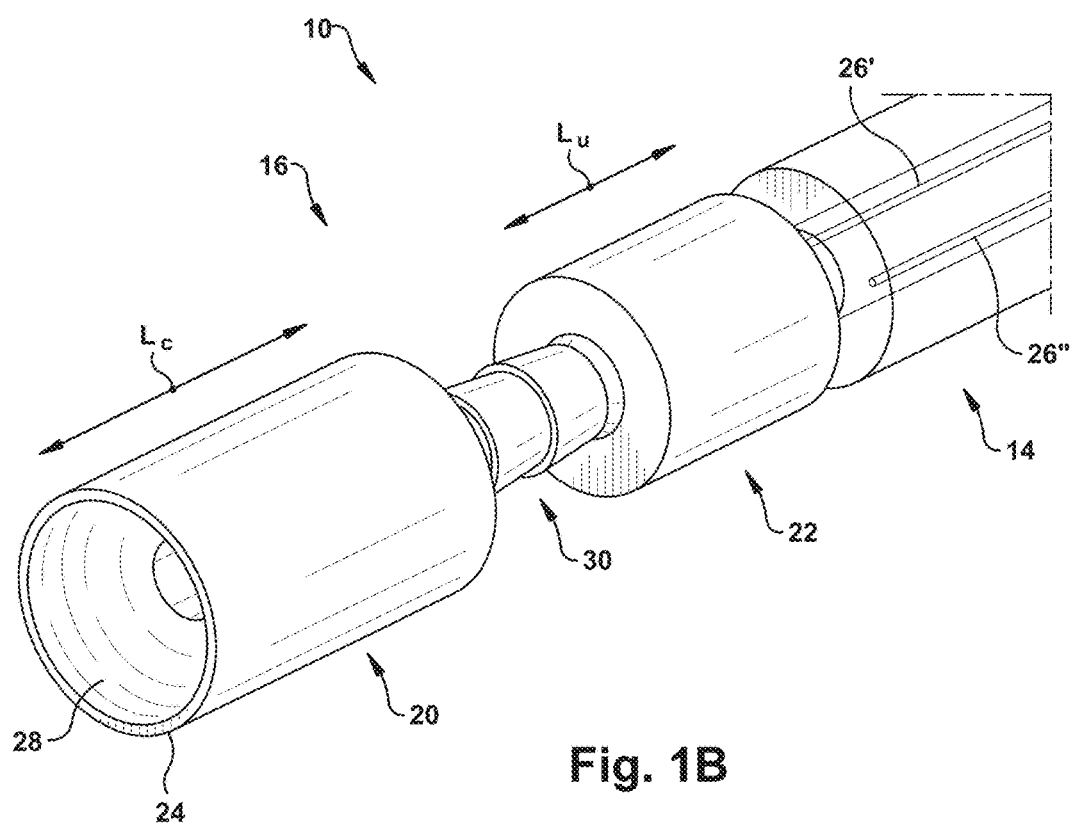

The present disclosure relates generally to devices and methods for removing biological tissue and, more particularly, to devices and methods for aspirating biological tissue utilizing acoustical waves during a surgical procedure. As representative of one aspect of the present disclosure, FIGS. 1A-B illustrate a device 10 for aspirating a biological tissue from a subject. Although the present disclosure is exemplified primarily in terms of devices and methods for collecting or aspirating bone marrow, one skilled in the art will appreciate that the present disclosure is in no way so limited, and that a variety of other device configurations and applications are also contemplated. For example, certain aspects of the present disclosure can include harvesting adipose tissue from less accessible or more lean areas. Other applications of the present disclosure can find use in cosmetic and reconstructive procedures as current methods for removing adipose and other tissues during such procedures rely on suction-based techniques, which can result in trauma or a reduced ability to adequately remove and/or sculpt the tissue to achieve a desired result. Additionally, certain aspects of the present disclosure can find use in harvesting tissue-specific stem cells from a target organ or tissue (e.g., skeletal muscle, smooth muscle, brain, kidney, cardiac, lung, pancreas, testis, skin, cartilage, placenta and bone), which may then be used to effectively treat damaged or diseased tissue from which the cells naturally reside (e.g., neuronal stem cells can be harvested from the brain to treat Parkinson's disease, while cardiac or smooth muscle cells may be harvested to treat heart disease). As current processes for harvesting tissue-specific stem cells are less than optimal (e.g., due to relatively low cell recovery rates and the time required to do so), certain aspects of the present disclosure can enhance retrieval of such tissues (and hence stem cells) in terms of both increased cell quantity and decreased collection time.

At present, bone marrow sampling in patients is done with a long, rigid needle and necessarily involves drilling multiple sites or holes in a target bone (e.g., pelvis) to obtain a sufficient amount of bone marrow. Due in large part to the necessity for multiple drill sites, conventional bone marrow harvesting techniques are very painful and highly time consuming as a sufficient amount of bone marrow is rarely collected from a single drill site. To overcome these drawbacks, the inventors of the present disclosure coupled an ultrasonic device to the tip of a semi-flexible shaft or needle, which was then used to deliver acoustical waves to bone marrow. It was surprisingly discovered that, upon applying the acoustical waves, bone marrow could be readily disrupted and aspirated without substantially damaging the cellular constituents thereof. Based at least in part on this discovery, the present disclosure advantageously provides devices and methods for harvesting sufficient quantities of a biological tissue (e.g., bone marrow or adipose tissue) from a single drill or entry site. Consequently, the post-procedure pain and time associated with harvesting a biological tissue is significantly diminished.

Devices

In one aspect of the present disclosure, a device for aspirating a biological tissue from a subject can generally comprise a flexible, hollow shaft connected at a distal end portion thereof to an ultrasound assembly. In some instances, the device can be configured for insertion through a delivery catheter. The shaft can have an elongated, tubular configuration and be made of one or a combination of polymeric materials. In one example, the shaft can have multilayer configuration consisting of a polyimide inner layer and a polyester block amide outer layer. The shaft can have a circular cross-sectional profile; however, it will be appreciated that other cross-sectional shapes are possible. Where the shaft has a circular cross-sectional profile, for example, the outer diameter (OD) can be less than about 3 mm to about 6 mm or more, and the inner diameter (ID) can be less than about 1 mm to about 2 mm or more.

The shaft can have a central portion that extends between a distal end portion and a proximal end portion. The shaft can include at least one lumen that extends between the distal and proximal end portions. The at least one lumen can be sized and dimensioned to receive and convey a disrupted biological tissue therethrough. The shaft can be selectively bendable in a transverse direction relative to a longitudinal axis, which extends between the proximal and distal end portions. In one example, the distal end portion of the shaft can be bendable up to about 35° relative to the longitudinal axis. In another example, the distal end portion of the shaft can be bendable up to about 45° relative to the longitudinal axis. The degree to which the distal end portion is bendable can depend upon the particular material(s) used to construct the shaft and/or the length of the shaft not covered by a delivery catheter. In some instances, the shaft can include an integral linear and/or rotational actuator mechanism that permits a user to selectively bend or move the shaft (e.g., the distal end portion) in an up-and-down and/or circular manner (respectively). Non-limiting examples of such actuator mechanisms can include DC motors, tactile pull wires, and the like. Advantageously, the ability to selectively bend or move the distal end portion of the shaft removes the need for multiple angular movements of the entire device, as well as multiple punctures to obtain the desired amount of biological tissue (e.g., bone marrow cells).

In another aspect, the ultrasound assembly of the device can be connected (e.g., directly connected) to the distal end portion of the shaft. In some instances, at least one ultrasound assembly can be directly connected to a distal end or tip of the shaft. In other instances, all or only a portion of at least one ultrasound assembly can be disposed within the distal end portion of the shaft. Since the ultrasound assembly is connected to the distal end portion of the shaft, the position of the ultrasound assembly relative to the longitudinal axis can be selectively adjusted or changed by bending or moving the shaft as discussed above.

The ultrasound assembly can generally comprise a casing, at least one ultrasound transducer disposed within the casing, and a second lumen that is in fluid communication with the at least one lumen of the shaft. Besides the at least one ultrasound transducer, the casing can be configured to house other components needed for operation of the device, such as a focusing element. In some instances, the casing can have a tubular configuration and include an annular leading edge adapted to contact the biological tissue. The annular leading edge can be sharpened or blunt. The casing can have a rigid configuration and be made of one or combination of medical grade metals or metal alloys, such as surgical steel or titanium. In some instances, the casing can include one or more radiopaque materials to facilitate visualization of the device, and in particular the ultrasound assembly, during use with appropriate imaging modalities.

The at least one ultrasound transducer can comprise any device, component, structure, or material that is capable of projecting acoustical waves or ultrasound energy. The at least one ultrasound transducer can sized and dimensioned so that the ultrasound transducer is entirely or partly disposed within the casing. Where the casing has a tubular configuration, for example, the at least one ultrasound transducer can have an annular or ring-shaped configuration. Additionally or optionally, at least one face or surface of the at least one ultrasound transducer can have a concave shape. In one example, the OD of the casing can be about 1 mm to about 3 mm. In some instances, the at least one ultrasound transducer can be comprised of one or a combination of materials having a resonant frequency range of about 200 kHz to about 5 MHz, and an actuator force of about 9N to about 900N or more. In other instances, the at least one ultrasound transducer can be a 1 MHz (e.g., 1.1 MHz) to a 9 MHz transducer. In one example, the at least one ultrasound transducer can be made of lead zirconate titanate (PZT), such as Navy Type I (PZT-4) or Navy Type II (PZT-5A).

One or more wires (e.g., microwires) can be connected to, and extend between, the at least one ultrasound transducer and a power source (e.g., a pulse generator). The wire(s) can extend from the at least one ultrasound transducer to the power source in a longitudinal or spiral manner. The wire(s) can be disposed within the lumen of the shaft and/or extend through the material comprising the shaft (e.g., between the inner and outer surfaces of the shaft). The wire(s) can be made of any one or combination of electrically conductive materials, such as copper (e.g., 30-40 gauge). Additionally or optionally, all or only a portion of the wire(s) can be insulated (e.g., coated) with a polyimide film. The wire(s) can be adapted to convey a range of input energies from the power source (e.g., about 10 mV to about 12 V). In one example, the wire(s) can be adapted to convey an input energy of greater than about 50 mV but less than about 80 mV. In some instances, the at least one ultrasound transducer can be a focused ultrasound transducer (e.g., high-intensity focused ultrasound or HIFU).

As mentioned above, the ultrasound assembly can also include a focusing element. The focusing element can generally have an annular or ring-shaped configuration and be disposed distal to the at least one ultrasound transducer within the casing. In some instances, the focusing element can be axially aligned, or arranged in parallel with, the at least one ultrasound transducer. The focusing element can include a concave focusing face that is configured for direct contact with a biological tissue. The pitch and/or surface area of the focusing face, as well as the material(s) used to form the focusing element, can be adjusted or customized to vary the focus and/or intensity of acoustical waves generated by the at least one ultrasound transducer. All or only a portion of the focusing element can be disposed within the casing. The focusing element can be made of one or a combination of materials, such as Parylene and polydimethylsiloxane. The materials used to construct the focusing element can be impedance-matched to permit efficient acoustic energy transfer from the at least one ultrasound transduces to the biological tissue. In some instances, the materials used to construct the focusing element and the casing can be impedance-matched. The focusing element and the at least one ultrasound transducer can at least partially define the second lumen of the ultrasound assembly.

It will be appreciated that devices of the present disclosure can include any one or combination of other features and/or components to facilitate efficient aspiration of biological tissue. In some instances, for example, devices of the present disclosure can include an irrigation mechanism configured to selectively dispense a fluid (e.g., sterile saline) therefrom. In such instances, the irrigation mechanism can include a third lumen that extends longitudinally through shaft and is in communication with a source of fluid. In other instances, devices of the present disclosure can be associated with a source of suction or negative pressure (e.g., a syringe) that facilitates withdrawal of a disrupted biological tissue therethrough. In further instances, devices of the present disclosure can include one or more sensors to detect when the ultrasound assembly reaches a biological tissue of interest (e.g., the bone marrow cavity). Other examples of features that may be included as part of the devices of the present disclosure can include optical elements (e.g., fiberoptics) to permit biological tissue visualization and/or a drive system for inducing vibrations in the ultrasound transducer and/or shaft.

Figure 7:
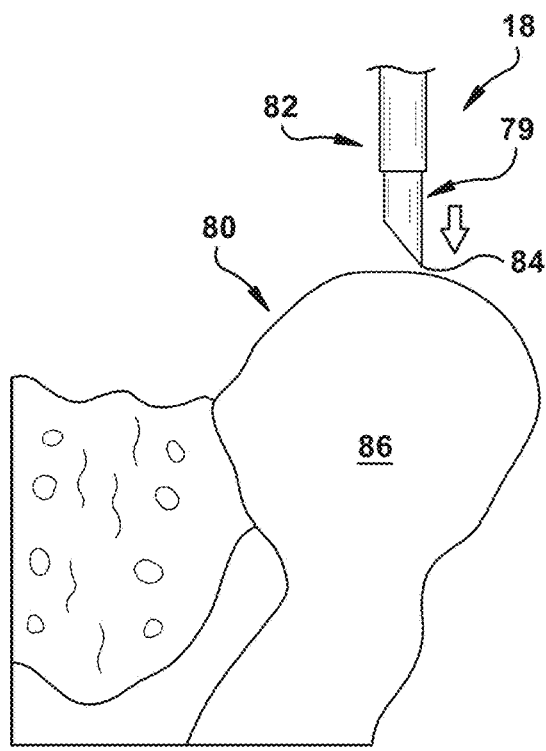
FIG. 7 is a schematic illustration showing a bore needle being positioned about an iliac crest of a subject.

One example of a device 10 for aspirating a biological tissue from a subject is illustrated in FIGS. 1A-B. The device 10 can comprise a flexible, hollow shaft 12 connected at a distal end 14 thereof to an ultrasound assembly 16. In some instances, the ultrasound assembly 16 can be directly connected to the distal end 14 of the shaft 12. The device 10 can be configured for insertion through a delivery catheter 18 (FIG. 7). The shaft 12 (FIGS. 1A-B) can have an elongated, tubular configuration and be made of one or a combination of polymeric materials. In one example, the shaft 12 can have multilayer configuration consisting of a polyimide inner layer and a polyester block amide outer layer. The shaft 12 can have a circular cross-sectional profile; however, it will be appreciated that other cross-sectional shapes are possible. Where the shaft 12 has a circular cross-sectional profile, for example, the OD can be less than about 3 mm to about 6 mm or more, and the ID can be less than about 1 mm to about 2 mm or more.

The shaft 12 can have a central portion (not shown) that extends between the distal end 14 and a proximal end (not shown) thereof. The shaft 12 can include a first lumen that extends between the distal end 14 and the proximal end. The first lumen can be sized and dimensioned to receive and convey a disrupted biological tissue therethrough. The shaft 12 can be selectively bendable in a transverse direction relative to a longitudinal axis, which extends between the proximal end and the distal end 14. In one example, the distal end 14 of the shaft 12 can be bendable up to about 35° relative to the longitudinal axis. In another example, the distal end 14 of the shaft 12 can be bendable up to about 45° relative to the longitudinal axis. The degree to which the distal end 14 is bendable can depend upon the particular material(s) used to construct the shaft 12 and/or the length of the shaft not covered by a delivery catheter. The shaft 12 can include an integral linear and/or rotational actuator mechanism (not shown) that permits a user to selectively bend or move the shaft (e.g., the distal end 14) in an up-and-down and/or circular manner (respectively). Non-limiting examples of such actuator mechanisms can include DC motors, tactile pull wires, and the like. Advantageously, the ability to selectively bend or move the distal end 14 of the shaft 12 removes the need for multiple angular movements of the entire device, as well as multiple punctures to obtain a desired amount of biological tissue (e.g., bone marrow cells).

In another aspect, the ultrasound assembly 16 of the device 10 can be connected to the distal end 14 of the shaft 12. Since the ultrasound assembly 16 is connected to the distal end 14 of the shaft 12, the position of the ultrasound assembly relative to the longitudinal axis can be selectively adjusted or changed by bending or moving the shaft as discussed above. The ultrasound assembly 16 can comprise a casing 20, at least one ultrasound transducer 22 disposed within the casing, and a second lumen that is in fluid communication with the first lumen of the shaft 12. In some instances, the casing 20 can have a tubular configuration and include a leading edge 24 adapted to contact a biological tissue. The leading edge 24 can have an annular shape and be sharpened or blunt. The casing 20 can have an OD that is less than, equal to, or greater than the OD of the shaft 12. In one example, the casing 20 can have an OD of about 2 mm to about 4 mm (e.g., about 3 mm). The casing 20 can have a length $L_c$ of about 2 mm to about 10 mm (e.g., about 5 mm) or more. The casing 20 can have a rigid configuration and be made of one or combination of medical grade metals or metal alloys, such as surgical steel or titanium. In some instances, the casing 20 can include one or more radiopaque materials (not shown) to facilitate visualization of the device 10, and in particular the ultrasound assembly 16, during use with an appropriate imaging modality.

Figure 3A:
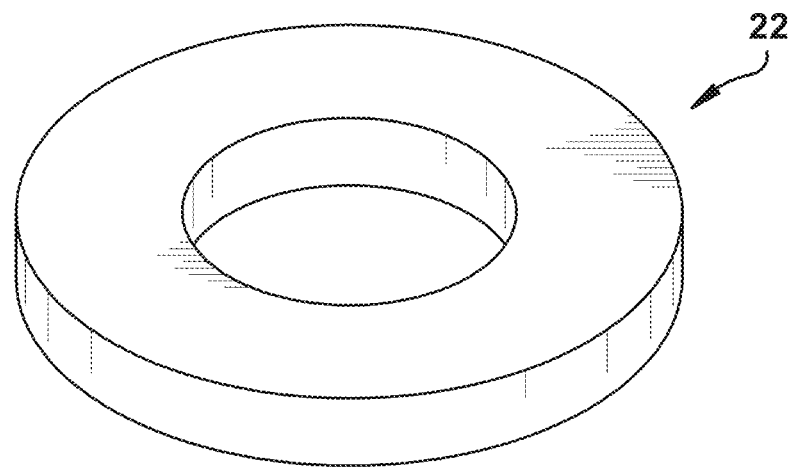
FIG. 3A is a perspective view of an ultrasound transducer comprising the ultrasound assembly in FIGS. 2A-B.
Figure 3B:
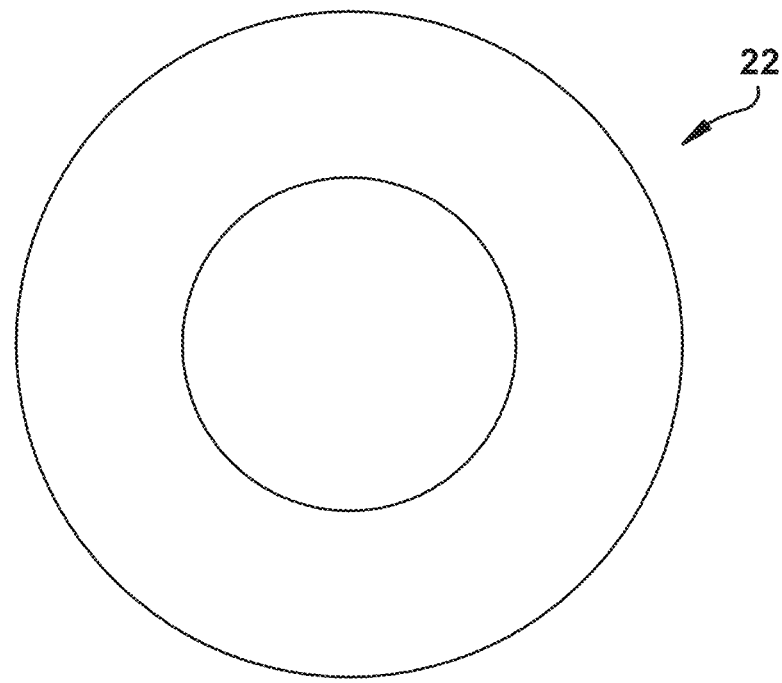
FIG. 3B is a plan view taken from the front of the ultrasound transducer in FIG. 3A.

The at least one ultrasound transducer 22 can comprise any device, component, structure, or material that is capable of projecting acoustical waves or ultrasound (ultrasonic) energy. The at least one ultrasound transducer 22 can be sized and dimensioned so that the ultrasound transducer is entirely or partly disposed within the casing 20. In one example, the at least one ultrasound transducer 22 can have a ring-shaped configuration (FIGS. 3A-B). Where the casing 20 (FIGS. 1A-B) has a tubular configuration, for example, the at least one ultrasound transducer 22 can have an annular or ring-shaped configuration. In one example, the OD of the at least one ultrasound transducer 22 can be about 2 mm to about 3 mm (e.g., about 2.65 mm to about 3 mm). In another example, the at least one ultrasound transducer 22 can have an ID of less than about 1 mm to about 3 mm (e.g., about 1.25 mm). In a further example, the at least one ultrasound transducer 22 can have an OD of about 1 mm. The at least one ultrasound transducer 22 can also have a length $L_u$ that is less than the length $L_c$ of the casing 20. In one example, the at least one ultrasound transducer 22 can have a length $L_u$ of about 2 mm to about 8 mm (e.g., about 3 mm to about 5 mm). In some instances, the at least one ultrasound transducer 22 can be comprised of one or a combination of materials having a resonant frequency range of about 200 kHz to about 5 MHz, and an actuator force of about 9N to about 900N or more. In other instances, the at least one ultrasound transducer 22 can be a 1 MHz (e.g., 1.1 MHz) to a 9 MHz transducer. In one example, the at least one ultrasound transducer 22 can be made of a PZT material, such as Navy Type I (PZT-4) or Navy Type II (PZT-5A). In some instances, the at least one ultrasound transducer 22 can be configured for use as a focused ultrasound transducer (e.g., HIFU).

One or more wires (e.g., microwires) can be connected to (e.g., directly connected), and extend between, the at least one ultrasound transducer 22 and a power source (e.g., a pulse generator). The wire(s) can extend from the at least one ultrasound transducer 22 to the power source in a longitudinal or spiral manner. As shown in FIGS. 1A-B, first and second wires 26' and 26" can extend biaxially along the longitudinal axis of the shaft 12. The first and second wires 26' and 26" can be disposed within the lumen of shaft 12 and/or extend through the material comprising the shaft (e.g., between the inner and outer surfaces of the shaft). The first and second wires 26' and 26" can be made of any one or combination of electrically conductive materials, such as copper (e.g., 30-40 gauge). Additionally or optionally, all or only a portion of the first and second wires 26' and 26" can be insulated (e.g., coated) with a polyimide film. The first and second wires 26' and 26" can be adapted to convey a range of input energies from the power source (e.g., about 10 mV to about 12 V). In one example, the first and second wires 26' and 26" can be adapted to convey an input energy of greater than about 50 mV but less than about 80 mV.

Figure 2A:
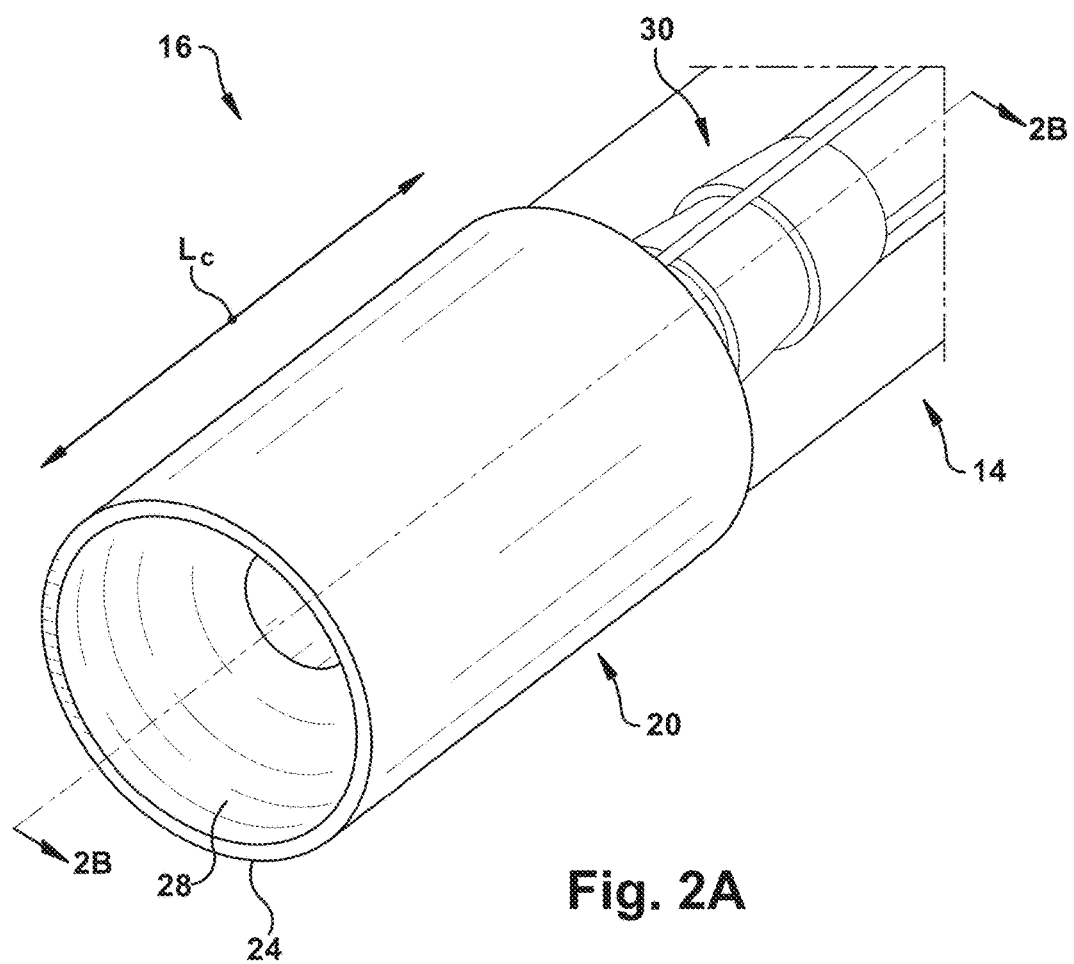
FIG. 2A is a magnified perspective view showing an ultrasound assembly comprising the device in FIGS. 1A-B.

In another aspect, the ultrasound assembly 16 (FIGS. 2A-B) can further include a focusing element 28 and a conduit 30 connected thereto. In some instances, the focusing element 28 and the conduit 30 can be directly connected to one another. For example, the focusing 28 element and the conduit 30 can be made of the same continuous material so as to form a single structure. Alternatively, the focusing element 28 and the conduit 30 can be made of the same or different material(s) and be directly connected to one another as two separately defined structures.

Figure 4A:
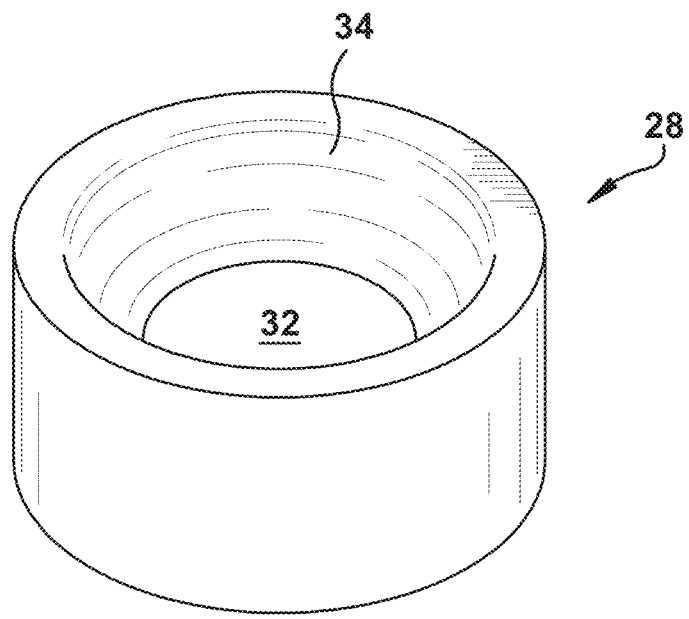
FIG. 4A is a perspective view showing a focusing element of the ultrasound assembly in FIGS. 2A-B.
Figure 4B:
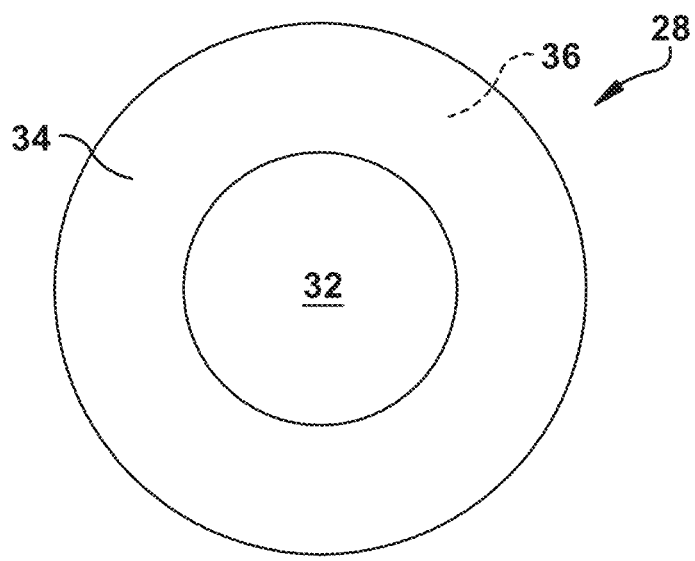
FIG. 4B is a plan view taken from the front of the focusing element in FIG. 4A.

As shown in FIGS. 4A-B, the focusing element 28 can have an annular or ring-shaped configuration and be disposed within the casing 20 so that it is located distal to the at least one ultrasound transducer 22. All or only a portion of the focusing element 28 can be disposed within the casing 20. The focusing element 28 can be axially aligned, or arranged in parallel with, the at least one ultrasound transducer 22. An aperture 32 or channel can extend between a focusing face 34 and a second surface 36 of the focusing element 28. The focusing face 34 can have a concave shape and be configured to directly contact a biological tissue. The pitch and/or surface area of the focusing face 34 can be varied as needed to optimize the focus and/or intensity of acoustical waves generated by the at least one ultrasound transducer 22. The focusing element 28 can be made of one or a combination of materials, such as Parylene and polydimethylsiloxane. The materials used to construct the casing 20 and the focusing element 28 can be impedance-matched. The focusing element 28 and the conduit 30 can at least partially define the second lumen of the ultrasound assembly 16.

Figure 2B:
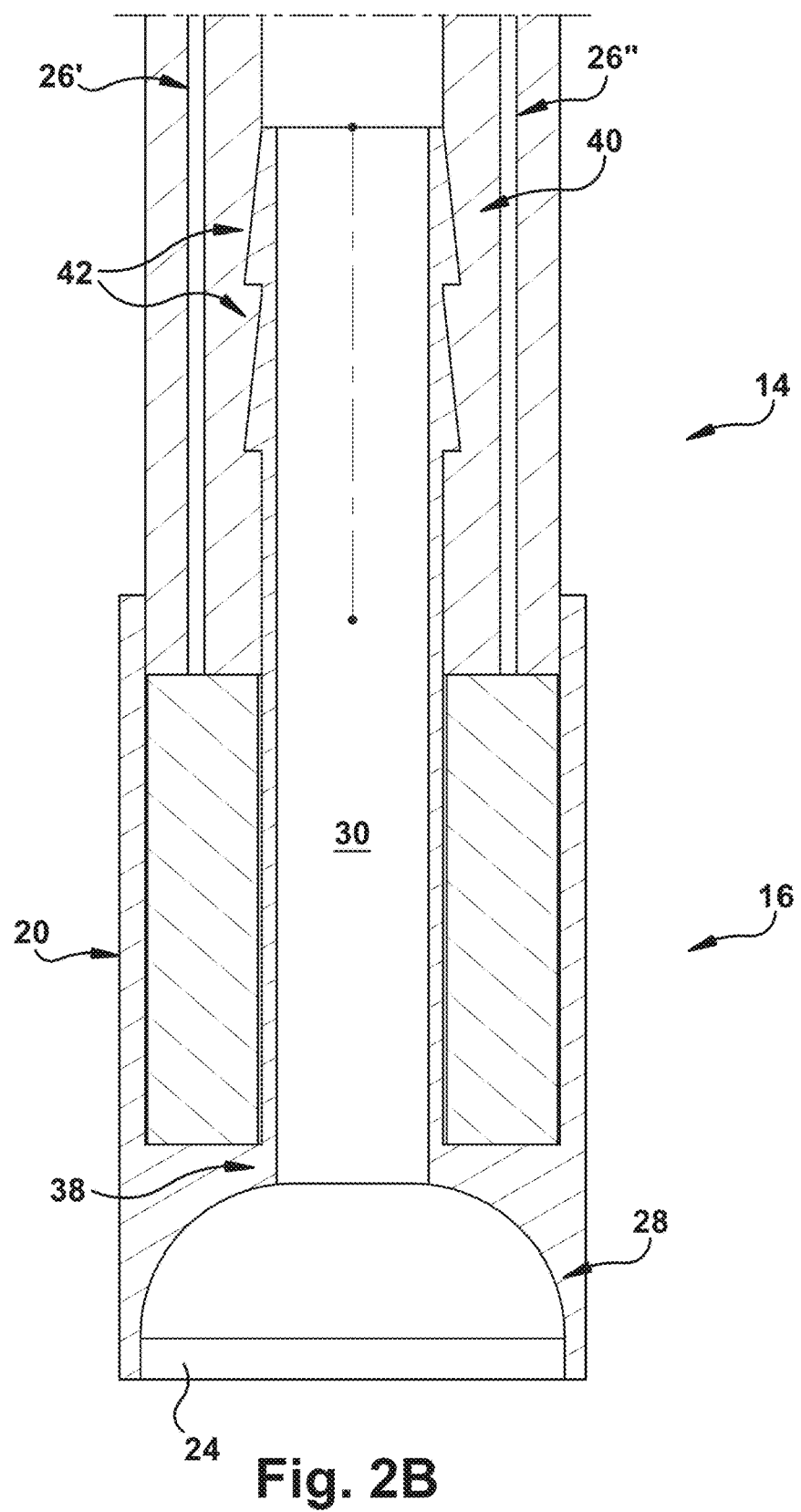
FIG. 2B is a cross-sectional view taken along Line 2B-2B in FIG. 2A.

Referring again to FIGS. 2A-B, the conduit 30 can have a generally tubular shape and include oppositely disposed first and second ends 38 and 40. The at least one ultrasound transducer 22 can be sized and dimensioned so that it is radially disposed about the conduit 30. In some instances, the second lumen of the ultrasound assembly 16 can extend between the first and second ends 38 and 40 of the conduit 30, as well as the aperture 32 of the focusing element 28. The first end 38 of the conduit 30 can be directly connected to the second surface 36 of the focusing element 28. The second end 40 of the conduit 30 can be adapted for insertion into the first lumen of the shaft 12. As shown in FIG. 2B, for example, the second end 40 of the conduit 30 can include a plurality of axially aligned, frustoconical mating members 42. The frustoconical shape of the mating members 42 facilitates a snug friction fit between an outer surface of the second end 40 and an inner surface defining the first lumen of the shaft 12. The mating members 42 can be formed from the same material as the rest of the conduit 30 or, alternatively, be separately defined structures situated about the second end 40 of the conduit.

Figure 5A:
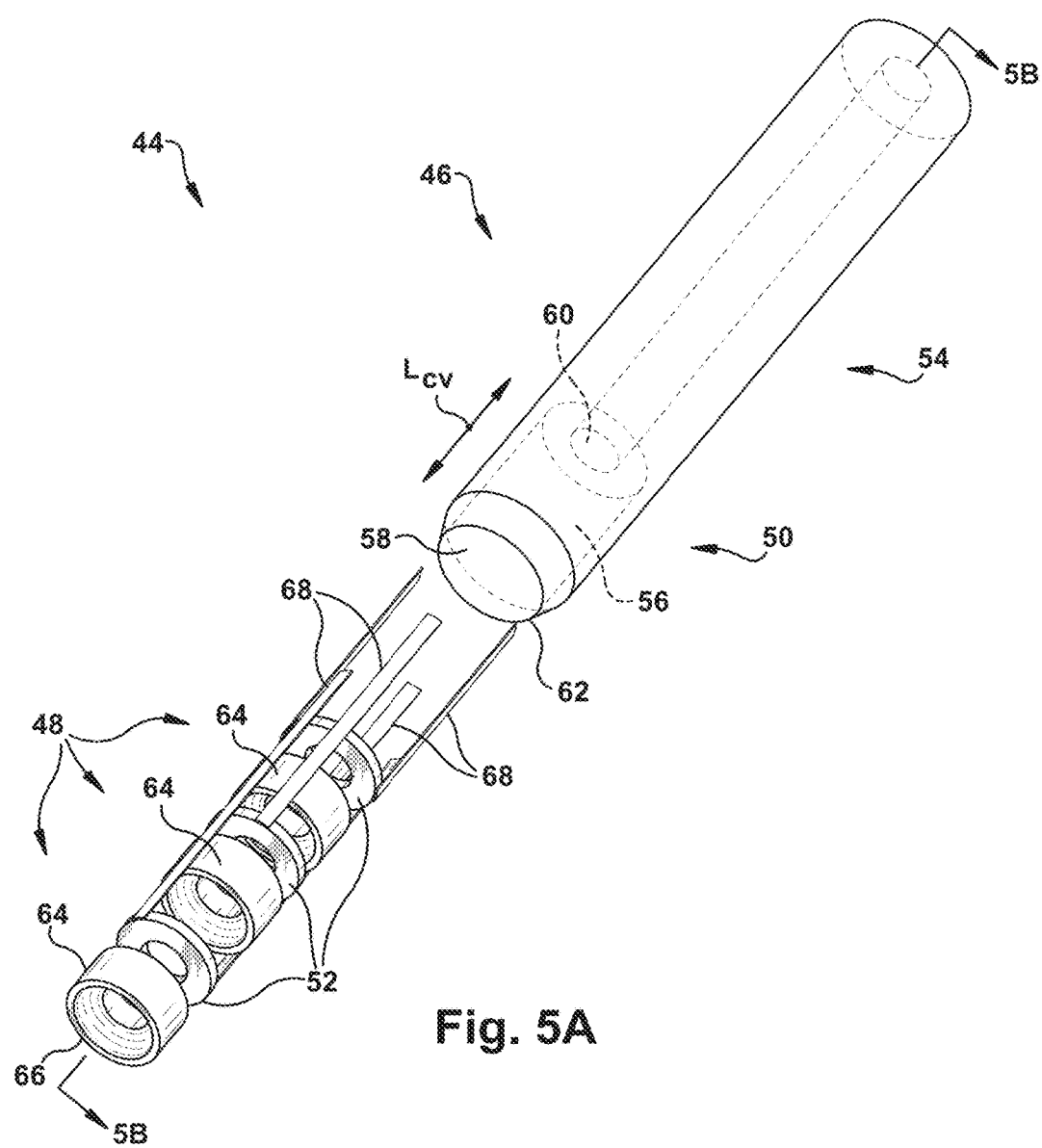
FIG. 5A is an exploded perspective view showing an alternative configuration of the device in FIGS. 1A-B constructed in accordance with another aspect of the present disclosure.
Figure 5B:
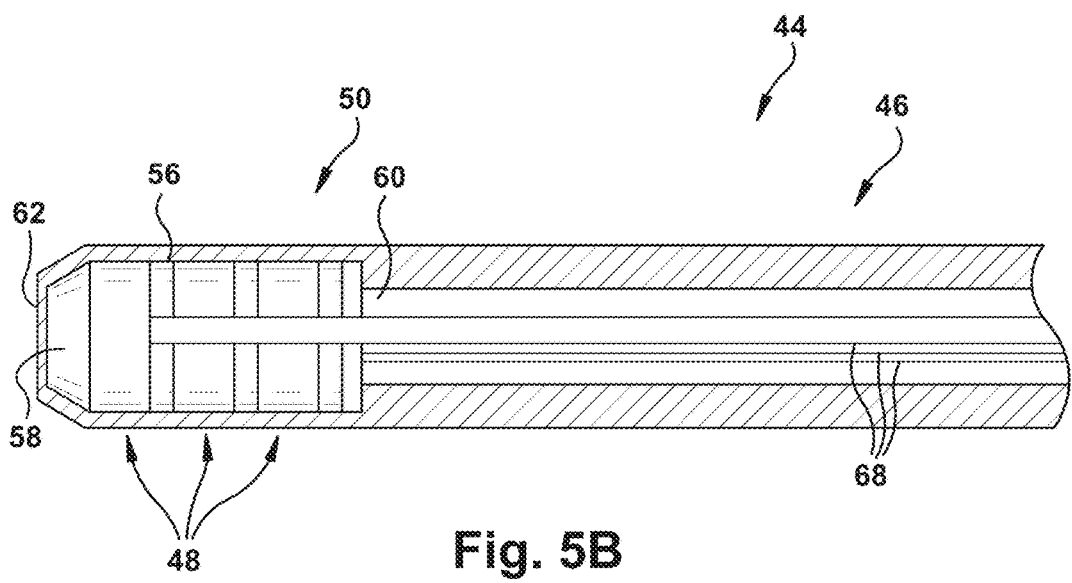
FIG. 5B is a cross-sectional view taken along Line 5B-5B in FIG. 5A showing the device in an assembled configuration.

Another example of a device 44 for aspirating a biological tissue from a subject is illustrated in FIGS. 5A-B. The device 44 can comprise a flexible, hollow shaft 46 and a plurality of axially aligned ultrasound assemblies 48 disposed within a distal end portion 50 of the shaft. The device 44 shown in FIGS. 5A-B includes three ultrasound assemblies 48; however, it will be appreciated that the device can include two, four, five, or more ultrasound assemblies. When disposed in the distal end portion 50 of the shaft 46, the ultrasound assemblies 48 can have a stacked or sandwiched configuration such that each of the ultrasound assemblies is parallel with the others. The parallel arrangement of ultrasound assemblies 48 within the distal end portion 50 of the shaft 46 can create a phased array such that an ultrasound transducer 52 of each of the ultrasound assemblies may be independently pulsed. By varying the timing (e.g., by pulsing the ultrasound transducers 52 one by one in sequence along a row), a pattern of constructive interference is set up that can result in a beam at a set angle, which can be steered electronically.

As shown in FIG. 5A, the shaft 46 can have a central body portion 54 that extends between a proximal end portion (not shown) and the distal end portion 50 thereof. A first lumen can extend between the proximal end portion and the distal end portion 50 of the shaft 46. The first lumen can be sized and dimensioned to receive and convey a biological tissue therethrough. The shaft 46 can have an elongated, tubular configuration and be made of one or a combination of polymeric materials. In one example, the shaft 46 can have multilayer configuration consisting of a polyimide inner layer and a polyester block amide outer layer. The shaft 46 can have a circular cross-sectional profile; however, it will be appreciated that other cross-sectional shapes are possible. Where the shaft 46 has a circular cross-sectional profile, for example, the OD of the shaft can be less than about 3 mm to about 6 mm or more, and the inner diameter ID of the shaft can be less than about 1 mm to about 2 mm or more.

The shaft 46 can be selectively bendable in a transverse direction relative to a longitudinal axis, which extends between the proximal end portion and the distal end portion 50. In one example, the distal end portion 50 of the shaft 46 can be bendable up to about 35° relative to the longitudinal axis. In another example, the distal end portion 50 of the shaft 46 can be bendable up to about 45° relative to the longitudinal axis. The degree to which the distal end portion 50 is bendable can depend upon the particular material(s) used to construct the shaft 46 and/or the length of the shaft not covered by a delivery catheter. The shaft 46 can include an integral linear and/or rotational actuator mechanism (not shown) that permits a user to selectively bend or move the shaft (e.g., the distal end portion 50) in an up-and-down and/or circular manner (respectively). Non-limiting examples of such actuator mechanisms can include DC motors, tactile pull wires, and the like. Advantageously, the ability to selectively bend or move the distal end portion 50 of the shaft 46 removes the need for multiple angular movements of the entire device 44, as well as multiple punctures to obtain the desired amount of biological tissue (e.g., bone marrow cells).

The distal end portion 50 of the shaft 46 can further include a recessed cavity 56 configured to receive the plurality of ultrasound assemblies 48. The cavity 56 can have a circular cross-sectional profile and extend between a first opening 58 and a second opening 60. The first opening 58 can be defined by a leading edge 62 (e.g., having an annular shape), which may be blunt or sharpened. The first opening 58 can have an ID that is greater than the ID of the second opening 60. In some instances, the ID of the second opening 60 can be equal to the ID of the first lumen. The cavity 56 can have an ID that is equal to, or about equal to, the OD of each of the ultrasound assemblies 48. Additionally, the cavity 56 can have a length $L_{cv}$ that is equal to, or about equal to, the collective length of the ultrasound assemblies 48 when stacked upon one another in the distal end portion 50 of the shaft 46.

In another aspect, each of the ultrasound assemblies 48 can comprise a casing 64, at least one ultrasound transducer 52, and a focusing element 66, each of which is partially or completely disposed within the casing. The plurality of ultrasound assemblies 48 can define a second lumen that is in fluid communication with the first lumen. The casing 64, focusing element 66, and at least one ultrasound transducer 52 of each of the ultrasound assemblies 48 can be identically or similarly constructed as the casing 20 (FIGS. 1A-B), the focusing element 28, and the at least one ultrasound transducer 22 described above.

As shown in FIGS. 5A-B, the ultrasound transducer 52 included as part of each ultrasound assembly 48 can include a wire 68 (e.g., a microwire) connected thereto. Each of the wires 68 can extend between a respective ultrasound transducer 52 and a power source (e.g., a pulse generator). The wires 68 can extend from each ultrasound transducer 52 to the power source in a longitudinal manner; however, it will be appreciated that other wire configurations (e.g., spiral) can be employed. As shown in FIG. 5B, the wires 68 can be disposed within the first lumen of shaft 46. The wires 68 can be made of any one or combination of materials, and be adapted to convey a range of input energies from the power source in a manner that is similar or identical to the first and second wires 26' and 26" (FIGS. 1A-B) described above.

Methods

Figure 6:
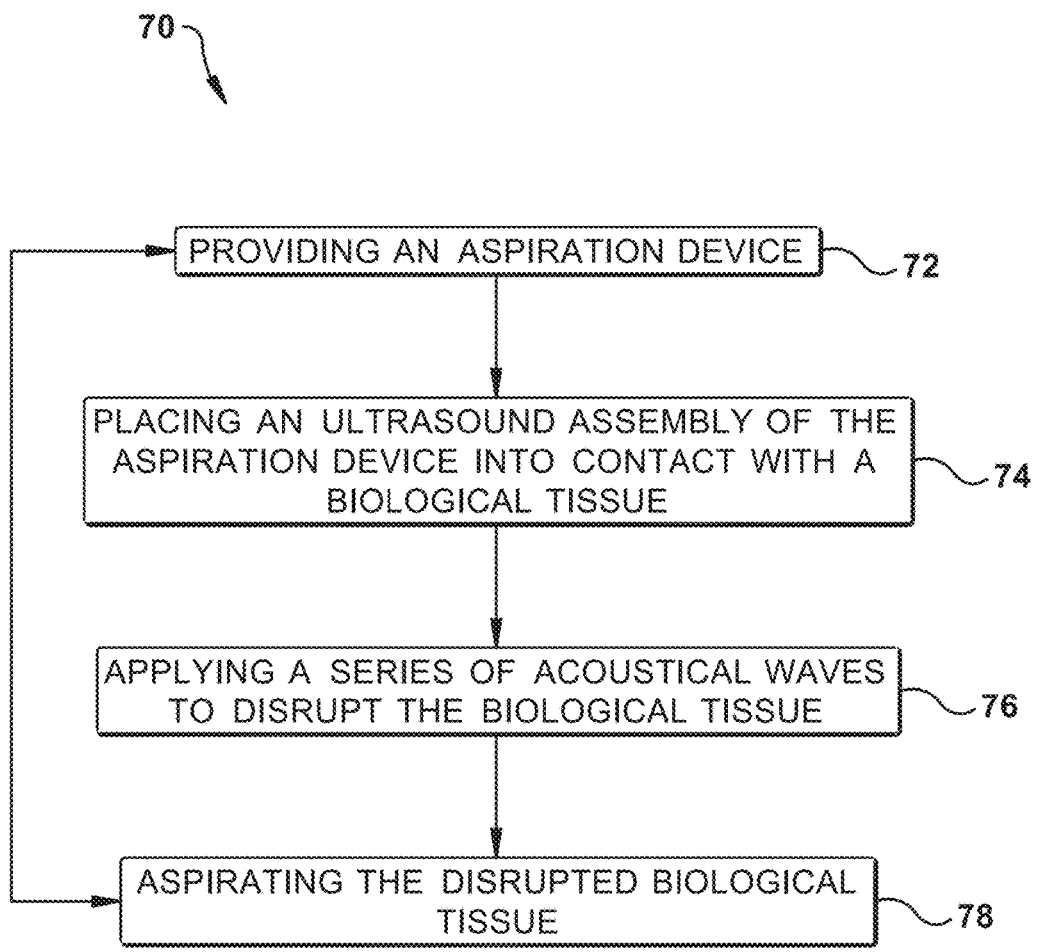
FIG. 6 is a process flow diagram illustrating a method for aspirating a biological tissue from a subject according to another aspect of the present disclosure.

Another aspect of the present disclosure can include a method 70 (FIG. 6) for aspirating a biological tissue from a subject. The method 70 can generally comprise the steps of: providing an aspiration device (Step 72); placing an ultrasound assembly of the aspiration device into contact with a biological tissue (Step 74); applying a series of acoustical waves to disrupt the biological tissue (Step 76); aspirating the disrupted biological tissue through the device (Step 78); and optionally repeating Steps 74-78 so that a new or different biological tissue is aspirated through the device. The method 70 can find use in a variety of surgical applications, such as bone marrow extraction, liposuction, stem cell collection/harvesting, etc. To this end, any one or combination of biological tissues can be harvested or aspirated from a subject, non-limiting examples of which are discussed above. As described in more detail below, the method 70 of the present disclosure can advantageously reduce pain associated with an aspiration procedure, improve efficiency of such procedures (e.g., by decreasing the required surgical time and the need for general anesthesia), and permit tailoring of the procedure to specific therapy requirements.

At Step 72, the method 70 can include providing an aspiration device. Aspiration devices suitable for use with the method can generally comprise a flexible, hollow shaft and an ultrasound assembly connected to a distal end of the device. The ultrasound assembly can comprise at least one ultrasound transducer, at least a portion of which is disposed within a casing. Non-limiting examples of aspiration devices 10 and 44 that may be used as part of the method 70 are illustrated in FIGS. 1A-5B and described above. The configuration of the aspiration device (e.g., shape, size, etc.) will depend on any number of factors, including the particular biological tissue to be aspirated, the amount of biological tissue needed, the time available for the aspiration procedure, the general health of the subject, etc. In one example, the device can be sized and dimensioned to facilitate a minimally invasive surgical aspiration procedure. It will be appreciated, however, that the device can be configured for other types of surgical approaches, including open, laparoscopic, and other percutaneous procedures.

After selecting an appropriate aspiration device, the ultrasound assembly of the device can be placed into contact with the target biological tissue (Step 74). Before doing so, and depending upon the particular biological tissue to be aspirated, the device can be loaded into a delivery catheter to facilitate delivery of the device to the biological tissue. Typically, an incision can be made in the skin of the subject to permit surgical access to the biological tissue. In instances where a laparoscopic approach is required, the device can first be inserted into a bodily orifice (e.g., mouth, nose, vagina or rectum). The device (and optionally the delivery catheter) can then be advanced towards the biological tissue. In some instances, use of the delivery catheter may be required to permit contact between the ultrasound assembly and the biological tissue (e.g., where a portion of bone must first be traversed to access bone marrow). In other instances, the ultrasound assembly may simply be passed through an incision or bodily orifice into direct contact with the biological tissue without the need to use a delivery catheter (or other surgical tool). In either case, the device can be placed at Step 74 so that the ultrasound assembly, and in particular the focusing element, is in direct contact with the biological tissue.

Next, a series of acoustical waves can be applied to the biological tissue to disrupt, but not substantially damage, the biological tissue (Step 76). To do so, a power source (e.g., pulse generator) can be activated to provide a desired input energy (or power) to the ultrasound transducer of the device. The input energy can be provided to the ultrasound transducer in a pulsed or continuous manner. A pulsed mode of operation, for example, may prevent heat build-up and reduce the likelihood of cavitation in the biological tissue, as well as help control the displacement effect of the ultrasound transducer. The input energy can be varied depending, for example, on the particular type and/or quantity of biological tissue to be aspirated. In some instances, the input energy can be less than about 10 mV to about 12 V (e.g., greater than about 50 mV (2 W) but less than about 80 mV (5 W)). Upon delivery of the input energy, the ultrasound transducer can generate a series of acoustical waves, which are then delivered to the biological tissue at a focal point a certain distance from the ultrasound assembly where peak ultrasound energy can be focused. The frequency and intensity of the delivered acoustical waves (or ultrasonic energy) can be tailored (e.g., to optimize the focal point) by selecting a desired input energy, a particular ultrasound transducer (e.g., size, shape, PZT material, etc.), and/or a particular focusing element configuration. Advantageously, the method 70 uses radiated, propogating acoustical waves (e.g., in short pulses) to disrupt the biological tissue into its cellular components, but without substantially damaging the tissue components.

At Step 78, a desired quantity of the disrupted biological tissue can be aspirated. To do so, suction or negative pressure can be applied to the device from a vacuum source, such as a syringe or mechanical pump. As suction is applied to the device, disrupted biological tissue can be aspirated through the second lumen of the ultrasound assembly into the first lumen of the shaft. The aspirated biological tissue can be collected in a sterile receptacle, where it can then be processed as needed.

Once substantially all of the disrupted biological tissue has been aspirated, Steps 74-78 of the method 70 can be repeated to harvest or collect a new or different biological tissue, but without the need to create another insertion or drill site. A user can manipulate the device, for example, by advancing it at different angular directions and/or at different depths so that the ultrasound assembly contacts a new (e.g., non-disrupted) or different biological tissue. When appropriately positioned, a series of acoustical waves can then be applied to the new biological tissue (as described above) to disrupt, but not substantially damage, the new biological tissue. As also described above, the disrupted biological tissue can be aspirated through the device. Steps 74-78 can be repeated any number of times until a sufficient amount of disrupted biological tissue is collected. Advantageously, a desired amount of biological tissue can be aspirated more efficiently, and with less post-procedure pain, than conventional aspiration methods, which require angular movements of the entire aspiration device and multiple punctures to obtain the desired amount of biological tissue.

One example of the method 70 is illustrated in FIGS. 7-12 and includes a method for harvesting bone marrow from a subject. Although FIGS. 7-12 illustrate one application of the method 70, it will be appreciated that the present disclosure is not so limited and, rather, that the method can find use in aspirating any one or combination of biological tissues.

Figure 8:
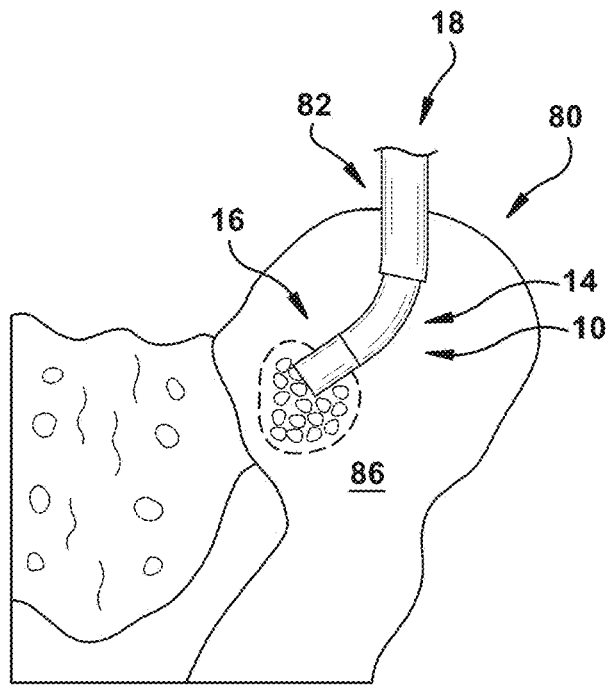
FIG. 8 is a schematic illustration showing the device in FIGS. 1A-B being deployed from a delivery catheter towards bone marrow after penetration of the bore needle (FIG. 7) into the iliac crest.

Referring to FIG. 7, a delivery catheter 18 containing a bore needle 79 can be percutaneously introduced and advanced to an iliac crest 80 of a subject. The distal tip 84 of the bore needle 79 can be brought into contact with the iliac crest 80, whereafter a sufficient amount of axial force is applied to the bore needle to penetrate through the cortex of the iliac crest and, optionally, advanced to a desired depth within the bone cavity so that it is at least partially immersed in the bone marrow 86. At this point, the bore needle 79 can be withdrawn from the delivery catheter 18, whereafter an aspiration device 10, such as the one illustrated in FIGS. 1A-B, is loaded into a proximal end (not shown) thereof and progressively advanced to a distal end 82 of the delivery catheter. The device 10 can then be urged through the distal end 82 of the delivery catheter 18 into contact with the bone marrow 86 (FIG. 8). If desired, the distal end 14 of the shaft 12 can be selectively controlled to bend in a transverse direction relative to the longitudinal axis of the shaft to appropriately position the ultrasound assembly 16.

Figure 9:
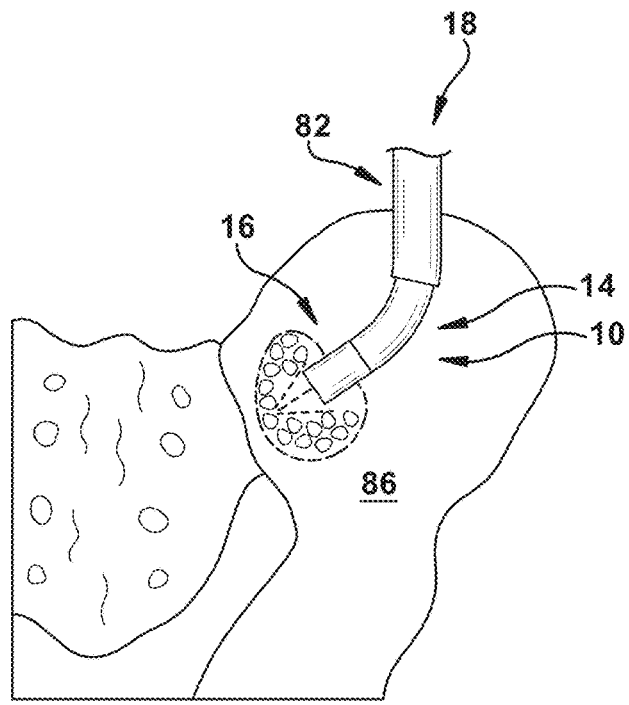
FIG. 9 is a schematic illustration showing the device in FIG. 8 applying a series of acoustical waves to the bone marrow.

Once the device 10 is appropriately positioned, a power source (e.g., pulse generator) can be activated to deliver a desired input energy (or power) to the ultrasound transducer 22 of the device in a pulsed or continuous manner. The input energy delivered to the ultrasound transducer 22 can be less than about 10 mV to about 12 V. In one example, the input energy delivered to the ultrasound transducer 22 can be greater than about 50 mV (2 W) but less than about 80 mV (5 W). Upon delivery of the input energy, the ultrasound transducer 22 can generate a series of acoustical waves, which are then delivered to the bone marrow 86 adjacent the ultrasound assembly 16 of the device 10 (FIG. 9). Delivery of the acoustical waves (e.g., in short pulses) to the bone marrow 86 can disrupt the bone marrow 86 into its cellular components (e.g., hematopoietic stem cells), but without substantially damaging the marrow components. Advantageously, the method permits application of acoustical waves to bone marrow 86 within a bone cavity, whereas external application of acoustical waves to a bone for the purpose of disrupting associated bone marrow would useless since ultrasound energy is absorbed by bone.

Figure 10:
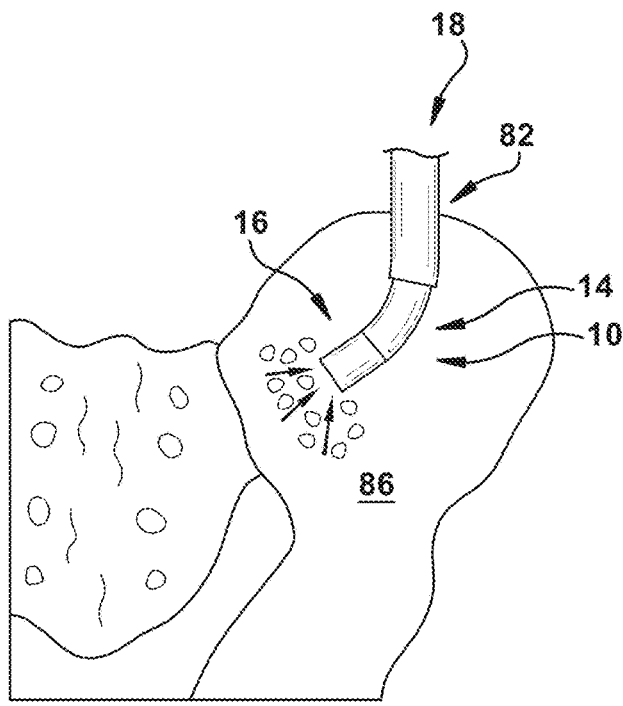
FIG. 10 is a schematic illustration showing bone marrow disrupted by the acoustical waves in FIG. 9 being aspirated through the device.
Figure 11:
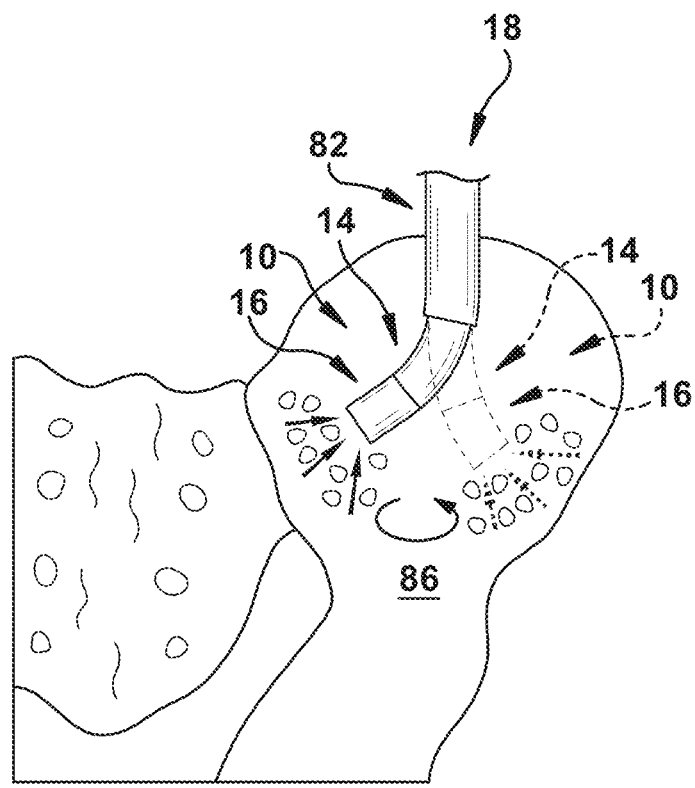
FIG. 11 is a schematic illustration showing the device in FIG. 10 being repositioned (indicated by dashed lines) to aspirate bone marrow from a different region of the bone cavity.

As shown in FIG. 10, suction can then be applied to the device 10 (e.g., using a syringe (not shown) coupled to the proximal end) so that the disrupted bone marrow 86 is aspirated through the device. When a sufficient amount of bone marrow 86 has been aspirated from a first region, the ultrasound assembly 16 of the device 10 may be rotated and moved to another region of the bone cavity for additional aspiration of bone marrow (FIG. 11). Aspiration of this new region may be repeated several times by advancing the ultrasound assembly 16 of the device 10 in different angular directions and/or at different depths into the bone marrow 86 containing spongy bone. This allows the device 10 to maximize the number of regions within the bone cavity for aspiration. Following movement of the ultrasound assembly 16 to another region, a series of acoustical waves can be applied (as described above) to the new region at a frequency and intensity sufficient to disrupt, but not substantially damage, the bone marrow 86. Advantageously, the desired amount of bone marrow cells can be aspirated more efficiently and with less post-procedure pain than with current aspiration systems, which require angular movements of the entire needle and multiple punctures to obtain the desired amount of bone marrow cells.

The following example is for the purpose of illustration only and is not intended to limit the scope of the claims, which are appended hereto.

Example

Two sets of experiments were conducted to evaluate the feasibility of the present disclosure in obtaining bone marrow harvests out of the operating room and in the clinic as an outpatient procedure with only local anesthesia required. The first set was focused on disruption of mice bone marrow to release more cells, and the second set was focused on testing the viability of the disrupted cells. The specialized ultrasonic instruments used in these experiments were a Sonic Concepts 1.1 MHz HIFU (Bothell, Wash.) with passive cavitation detection, and an E&I RF amplifier (Rochester, N.Y.). A high-frequency power generator was used to send variable power input to the 1.1 MHz HIFU. LabVIEW software (National Instruments, Inc., Austin, Tex.) was used to control the power generator. The user interface had a start/stop function as well as a power level function. The power level was labeled Vpp in the user interface, and sent out a signal (in mV) to the generator, which was translated into a power setting. For example, an entered Vpp value of 50 mV was translated by the generator and sent to the HIFU as 2 W of power.

Disruption tests were carried out using the HIFU on mice marrow. Mice leg bones were freshly harvested and splayed open to expose marrow. A power ranging from <1 W to 5 W for a duration of 10 second was then transmitted to the marrow. The following procedure was employed for the disruption tests: (1) fill transducer cone vessel to top (top is the focal point) with water; (2) attach parafilm tightly across focal point opening on the cone vessel; (3) using a pipette, transfer 20 μL of Phosphate Buffer Solution (PBS) onto the center of the opening; (4) place bone with the marrow face down over the center and hold gently down with tweezers as the bone will have a tendency to shift during the test; (5) set power on the computer and start the test (run test for duration of 10 seconds); (6) collect PBS solution with pipette and put in a vial; (7) remove bone and wash the parafilm with ethanol; and (8) repeat steps (3)-(7) for each power setting. After all the tests were completed, a hemacytometer and microscope were used to count the number of cells for each test sample. The concentration of cells counted was used to indicate the effectiveness of bone marrow disruption.

Figure 12:
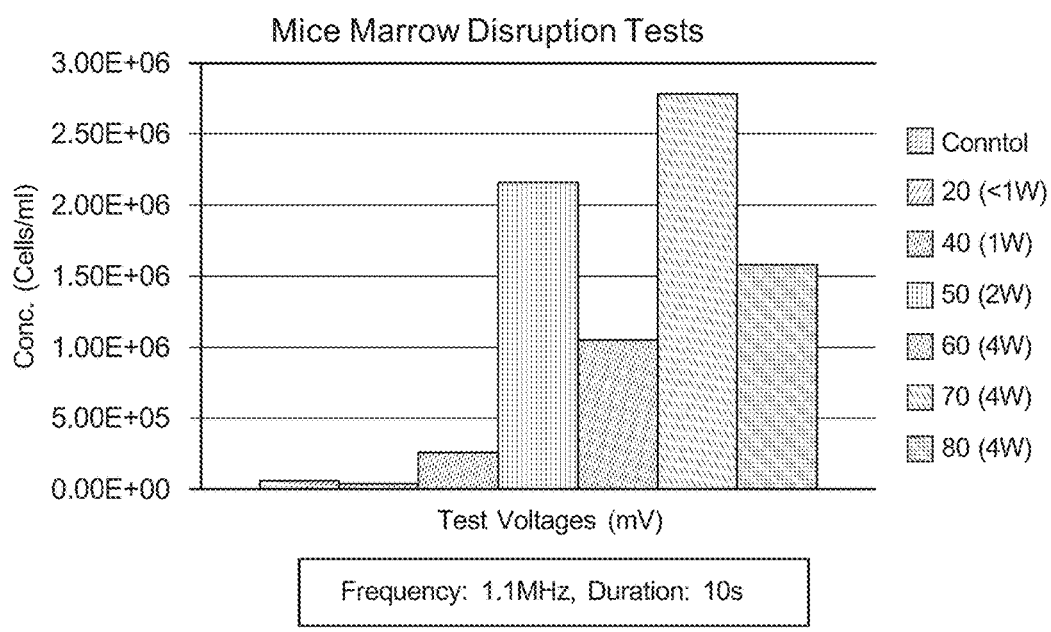
FIG. 12 is a graph showing the results of mice marrow disruption tests in which test voltages (mV) are plotted against cell concentration (cells/ml)

Our hypothesis for the mouse bone marrow disruption tests was that after a critical power was reached, we would see a sharp increase in disruption followed by a plateau. Disruption test results are shown in FIG. 12. The test results indicate that for our experimental set-up, the input Vpp of 50 mV (2 W) is significant because there is an observable dramatic increase in disruption. There are no other dramatic jumps in disruption at higher powers.

Cell viability tests were conducted in the same manner as the mice marrow disruption tests. The only difference was the additional step of mixing 10 μL of sample with 10 μL of Trypan Blue before using the hemacytometer. Trypan blue is stain that live cells, because they have functioning membranes, will not absorb. Dead cells, on the other hand, will be stained. Cell counting was done on a viable cell versus dead cell basis. It is also worth noting that only freshly harvested marrow worked for cell viability tests.

Figure 13:
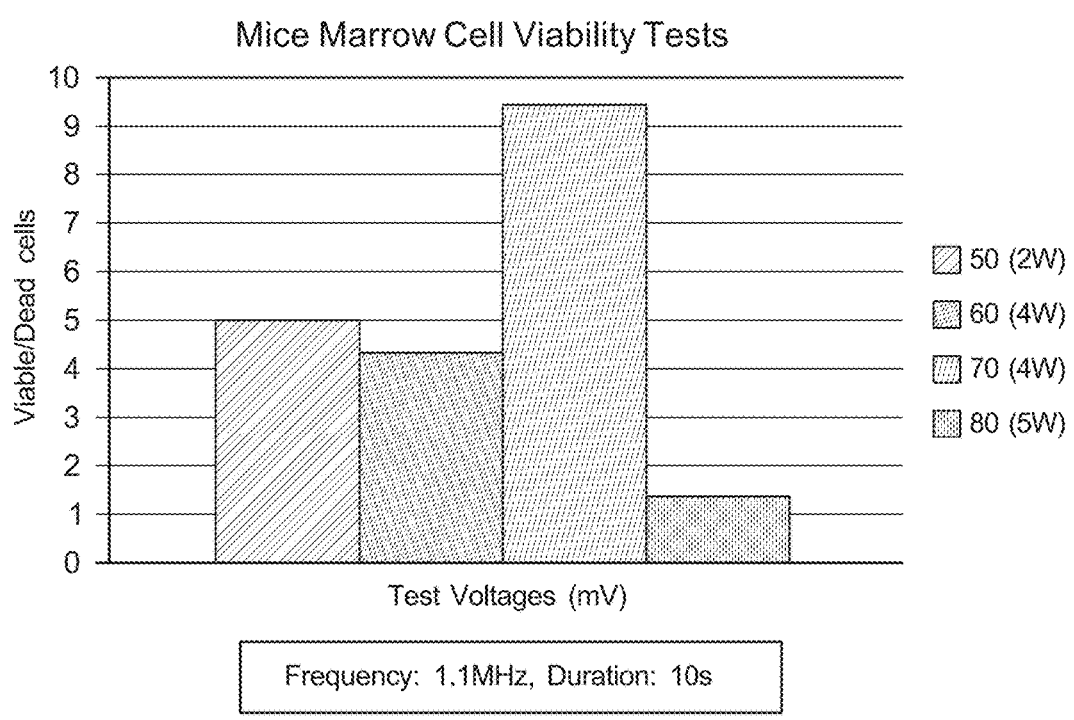
FIG. 13 is a graph showing the results of mice marrow cell viability tests in which test voltages (mV) are plotted against the ratio of viable to dead cells.

Our hypothesis for the cell viability tests was that we would find a critical power where we see a dramatic increase in cell death. The hope was that critical power that killed cells would be above the critical power where high disruption began to occur. This would be the first assessment to see if disruption without cell destruction would be possible. Cell viability test results are shown in FIG. 13. The test results showed a dramatic increase in cell death at an input Vpp of 80 mV (5 W). This is above the critical cell disruption power, Vpp of 50 mV (2 W), and thus high-frequency, high power, ultrasound can be used to loosen cells without killing a large portion of the cell population.

From the above description of the present disclosure, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

The following is claimed:

1. An intra-osteal device for aspirating a viable biological tissue from a subject, the device comprising:
    a flexible, hollow shaft having a central portion that extends between a proximal end of the shaft and a distal end of the shaft, the shaft including a first lumen that extends between the proximal end of the shaft and the distal end of the shaft; and
    an ultrasound assembly that is connected to, and extends distally from, the distal end of the shaft, the ultrasound assembly including a casing, a focusing element that is disposed within the casing and adapted for direct contact with the biological tissue, at least one ultrasound transducer disposed within the casing, and a second lumen that extends through each of the casing, the focusing element, and the at least one ultrasound transducer such that the second lumen is in fluid communication with the first lumen;
    wherein the at least one ultrasound transducer is configured to generate acoustical waves having an intensity and frequency sufficient to disrupt the biological tissue, when the focusing element is placed in direct contact with the biological tissue, so that the biological tissue remains viable when aspirated through the first lumen;
    wherein the focusing element comprises a material that is acoustical impedance matched to the casing;
    wherein the ultrasound assembly further comprises a conduit including oppositely disposed first and second ends that define the second lumen, wherein the first end comprises an opening in fluid communication with an aperture of the focusing element, and the second end is adapted for insertion into the first lumen of the shaft;
    wherein the focusing element is ring-shaped and has a concave surface configured to be placed in direct contact with the biological tissue;
    wherein the focusing element is located at a distal end of the casing:
    wherein each of the focusing element and the ultrasound transducer is entirely disposed within the casing.

2. The device of claim 1, wherein the at least one ultrasound transducer is a high-intensity focused ultrasound (HIFU) transducer.

3. The device of claim 1, wherein energy delivered to the at least one ultrasound transducer from a power source is greater than about 10 mV but less than about 12 V.

4. The device of claim 3, wherein the energy delivered to the at least one ultrasound transducer is greater than about 50 mV but less than about 80 mV.

5. The device of claim 1, wherein the conduit extends through the at least one ultrasound transducer such that the at least one ultrasound transducer is radially disposed about at least a portion of the conduit.

6. The device of claim 1, wherein the focusing element is shaped for placement into direct contact with bone marrow, and the focusing element includes an aperture extending therethrough.

7. The device of claim 1, wherein the casino has an annular leading edge adapted to directly contact the biological issue.

8. The device of claim 1, wherein a conduit extends between, and is directly connected to each of, the focusing element and the ultrasound transducer.

9. A method for harvesting viable bone marrow from a subject, the method comprising the steps of:
(a) providing a device that includes a flexible, hollow shaft and an ultrasound assembly that is connected to, and extends distally from, a distal end of the shaft, the ultrasound assembly comprising at least one ultrasound transducer and a focusing element disposed in a casing, the device further including a first lumen that extends between a proximal end and a distal end of the shaft, wherein the ultrasound assembly includes a second lumen that extends through each of the casing, the focusing element, and the at least one ultrasound transducer such that the second lumen is in fluid communication with the first lumen, wherein each of the focusing element and the ultrasound transducer is entirely disposed within the casing;
(b) inserting the device through an insertion site that extends through a cortical bone portion of a bone so that the focusing element is in direct contact with bone marrow of the bone;
(c) applying, after directly contacting the focusing element with the bone marrow, a series of generated acoustical waves to loosen the bone marrow, the acoustical waves being generated using a critical input power, Vpp, of greater than 50 mV and less than 80 mV; and
(d) aspirating at least a portion of the loosened bone marrow through the flexible shaft of the device, wherein the aspirated bone marrow is viable wherein steps (c)-(d) are repeated without having to create another insertion site in the bone.

* * * * *